US010254107B1

(12) United States Patent
Faville et al.

(10) Patent No.: US 10,254,107 B1
(45) Date of Patent: Apr. 9, 2019

(54) ELLIPSOMETER APPARATUS HAVING MEASUREMENT COMPENSATION

(71) Applicant: Falex Corporation, Sugar Grove, IL (US)

(72) Inventors: Andrew Faville, Geneva, IL (US); Michael S. Feltman, Sugar Grove, IL (US)

(73) Assignee: Falex Corporation, Sugar Grove, IL (US)

( * ) Notice: Subject to any disclaimer, the term of this patent is extended or adjusted under 35 U.S.C. 154(b) by 0 days.

(21) Appl. No.: 15/486,069

(22) Filed: Apr. 12, 2017

Related U.S. Application Data

(60) Provisional application No. 62/321,205, filed on Apr. 12, 2016.

(51) Int. Cl.
*G01B 11/06* (2006.01)
*G01N 21/21* (2006.01)

(52) U.S. Cl.
CPC ........ *G01B 11/0641* (2013.01); *G01N 21/211* (2013.01); *G01N 2201/06113* (2013.01)

(58) Field of Classification Search
CPC .............. G01B 11/0641; G01N 21/211; G01N 2201/06113
USPC ........................................................ 356/369
See application file for complete search history.

(56) References Cited

U.S. PATENT DOCUMENTS

| 4,210,401 A | 7/1980 | Batten |
| 4,842,410 A * | 6/1989 | Darrah .............. G01B 11/0675 356/505 |
| 5,223,718 A | 6/1993 | Taboada |
| 5,293,218 A | 3/1994 | Morris et al. |
| 5,754,296 A * | 5/1998 | Law ..................... G01B 11/065 356/369 |
| 5,764,365 A * | 6/1998 | Finarov ............... G01B 11/065 356/369 |
| 6,657,708 B1 | 12/2003 | Drevillon et al. |
| 7,088,448 B1 | 8/2006 | Hahn et al. |
| 7,280,209 B2 | 10/2007 | Strocchia-Rivera |
| 7,768,660 B1 * | 8/2010 | Pribil .................... G01N 21/55 356/237.1 |
| 2005/0095731 A1 * | 5/2005 | Mantz ................. G01N 21/211 438/16 |
| 2015/0292866 A1 | 10/2015 | Sasaki et al. |

OTHER PUBLICATIONS

Samuel Tucker Browne, et al., Enhancement of Aviation Fuel Thermal Stability Characterization Through Application of Ellipsometry, National Aeronautics and Space Administration, NASA/TM-2012-217404, Jan. 3, 2012.

* cited by examiner

*Primary Examiner* — Hina F Ayub
(74) *Attorney, Agent, or Firm* — Paul J. Nykaza; Tejpal S. Hansra

(57) ABSTRACT

An ellipsometer apparatus (10) has a measurement compensation feature. The ellipsometer (10) provides for relative lateral movement between a light source assembly (12) and a specimen holder (14) via a positioner assembly (16) to provide for more accurate measurements of a thin film layer (55) on a specimen member (50).

12 Claims, 7 Drawing Sheets

ELLIPSOMETER APPARATUS HAVING MEASUREMENT COMPENSATION

CROSS-REFERENCE TO RELATED APPLICATIONS

The present application claims the benefit of U.S. Patent Application No. 62/321,205 filed on Apr. 12, 2016, which application is incorporated by reference herein.

FEDERALLY SPONSORED RESEARCH OR DEVELOPMENT

None.

TECHNICAL FIELD

The invention relates generally to an ellipsometer apparatus and, in particular, to an ellipsometer apparatus having a measurement compensation feature.

BACKGROUND OF THE INVENTION

Ellipsometry is an optical technique used to investigate properties of a specimen sample. Generally, ellipsometry may be defined as the measurement of the state of polarized light waves. An ellipsometer apparatus is known in the art and measures the changes in the polarization state of light when it interacts with a specimen sample. The ellipsometer apparatus is used in many different areas including physics, chemistry, materials science, biology, mechanical engineering, metallurgical engineering and biomedical engineering. One particular area where ellipsometers are used is in investigating properties of thin films on a specimen sample such as by measuring a thickness of a thin film formed on a surface of the specimen sample. Other properties can also be determined such as volume, chemical composition, roughness, index of refraction and electrical conductivity.

One specific application of ellipsometers is in evaluating the physical properties of fuels, such as in thermal oxidation testing of jet fuels. Jet fuels are subjected to thermal stress in the operation of an aircraft due to designs that utilize jet fuel as a coolant in various heat exchangers used in jet engine systems. These thermal stresses can affect the performance of the fuel. Fuel manufacturers continue in their efforts to develop more thermally stable jet fuels as well as enhance their ability to better test the thermal stability of jet fuels.

The American Society for Testing and Materials (ASTM) developed a test, commonly referred to as The Jet Fuel Thermal Oxidation Test that is widely used to determine the thermal stability of jet fuels. The test, as designated by ASTM D3241, is the standardized test procedure used to assess the thermal stability of conventional jet fuels. As part of this test, jet fuel is first passed over a specimen sample in the form of a heated metal tube. The thermal stability of the fuel is characterized by the amount of deposits adhering to the tube. The deposits form a thin film and thus, the thickness of the thin film is an indication of the thermal stability of the fuel. The ellipsometer apparatus is then used to determine the film thickness and determine the thermal stability of the jet fuel.

When preparing the tube sample to be analyzed in the ellipsometer, the tube can sag, bend or warp or otherwise become distorted. The tube is typically formed from aluminum or stainless steel and the heat applied to the tube in conjunction with the fuel being passed over the tube sometimes results in bending of the tube. Such bends or distortions can affect the ellipsometer analysis and consequently the accuracy of the measurements taken by the ellipsometer. For example, a most accurate film thickness measurement is determined by the ellipsometer at the bottom center of the specimen tube. Thus, the beam of light from the light source assembly is directed to the bottom center of the specimen tube. If the specimen tube is bent, warped etc., the beam of light will not be directed at the actual true bottom center of the specimen tube. Accordingly, film thickness measurements will be off or inaccurate. Because the ellipsometer is capable of measuring down to extremely minute thicknesses, even a slight bend in the tube can significantly affect the accuracy of measurements taken by the ellipsometer. Efforts have been made to straighten the tube samples prior to mounting the tubes in the ellipsometer. These straightening techniques, however, have led to other problems such as broken tubes or discontinuity of the thin film being measured. Current ellipsometers do not have any mechanisms to compensate for such tube shape distortions or deviations.

While such ellipsometers according to the prior art provide a number of advantageous features, they nevertheless have certain limitations. The present invention is provided to overcome certain of these limitations and other drawbacks of the prior art, and to provide new features not heretofore available. A full discussion of the features and advantages of the present invention is deferred to the following detailed description, which proceeds with reference to the accompanying drawings.

SUMMARY OF THE INVENTION

The present invention provides an ellipsometer having measurement compensation in the form of an automatic tube centering feature.

According to a first aspect of the invention, a positioner assembly is capable of lateral movement with respect to a light source assembly to provide for measurements along a lateral portion of a specimen member in the form of a specimen tube. This feature allows for measurements to be taken at the desired bottom center of the tube even if the tube is bent or warped etc. Measurements taken at a plurality of lateral measurement locations allows for the determination of the true bottom center of the specimen tube.

According to another aspect of the invention, an ellipsometer apparatus analyzes a film layer on a specimen member defining a test surface. The apparatus has a light source assembly having a laser emitter and a laser receiver, and a specimen holder configured to hold the specimen member. A positioner assembly is connected to the specimen holder and the positioner assembly has a first positioner capable of moving the specimen holder along a first longitudinal axis. The positioner assembly also has a second positioner capable of moving the specimen holder along a second lateral axis. A controller is operably connected to the light source assembly and the positioner assembly wherein the laser emitter is configured to project a beam of light onto the test surface wherein the beam of light is deflected by the test surface and wherein the laser receiver is configured to receive the deflected beam of light wherein a film thickness measurement is determined by the controller. The controller is capable of determining a plurality of film thickness measurements at a plurality of longitudinal measurement locations along the first longitudinal axis and at a plurality of lateral measurement locations along the second lateral axis.

According to a further aspect of the invention, at a first longitudinal measurement location, the controller is capable of determining a plurality of film thickness measurements along the second lateral axis. The controller is also capable of determining a greatest film thickness value among the plurality of thickness measurements determined along the second lateral axis wherein the controller assigns the greatest film thickness value to the first longitudinal measurement location.

According to a further aspect of the invention, the specimen member is a cylindrical tube and the greatest film thickness value corresponds to the film thickness at a bottom center location on the tube.

According to a further aspect of the invention, at each one of the plurality of longitudinal measurement locations, the controller determines a plurality of film thickness measurements along the second lateral axis.

According to a further aspect of the invention, the first positioner has a first positioner motor connected to a first lead screw. The first lead screw is operably connected to the specimen holder, wherein the first lead screw is rotatable by the first positioner motor to move the specimen holder along the first longitudinal axis. The second positioner has a second positioner motor connected to a second lead screw. The second lead screw is operably connected to the specimen holder, wherein the second lead screw is rotatable by the second positioner motor to move the specimen holder along the second lateral axis. The second lateral axis is generally transverse to the first longitudinal axis.

According to another aspect of the invention, the positioning assembly further has a rotary positioner operably connected to the specimen holder and is configured to rotate the specimen member 360° around a central axis of the specimen member wherein the specimen member is a tube wherein the test surface is cylindrical.

According to another aspect of the invention, the specimen member is a tube defining a cylindrical test surface wherein, at the longitudinal measurement location, the controller is configured to determine a plurality of film thickness measurements along the lateral axis and along a periphery of the tube. The controller is further configured to determine the greatest film thickness measurement along the lateral axis to be a bottom center of the tube. The controller assigns the greatest film thickness measurement to the longitudinal measurement location.

According to a further aspect of the invention, the specimen member is a cylindrical member defining a cylindrical test surface, wherein a plurality of measurements taken on the specimen member along the first longitudinal axis defines a slice of measurements, and wherein measurements are taken on the specimen member corresponding to a plurality of slices around the cylindrical specimen member.

According to a further aspect of the invention, structures are disclosed for providing relative movement in a first longitudinal direction and, independently, in a second lateral direction, between the specimen holder and the light source assembly. The laser emitter emits a light beam that is reflected by the specimen tube and received by the laser receiver wherein in cooperation with a controller, a film thickness is determined at a plurality of longitudinal measurement locations and at a plurality of lateral measurement locations.

According to a further aspect of the invention, the controller is operably connected to the light source assembly and the positioner assembly wherein the laser emitter is configured to project a beam of light onto the test surface at a measurement location wherein the beam of light is deflected and configured to be received by the laser receiver wherein a film thickness measurement is determined by the controller. The positioner assembly is configured to move the specimen tube along the lateral axis wherein a plurality of film thickness measurements are determined by the controller along the test surface of the tube along the lateral axis.

According to another aspect of the invention a method of analyzing a thin film on a specimen tube defining a cylindrical test tube wherein the controller is capable of determining a plurality of film thickness measurements at a plurality of longitudinal measurement locations along the first longitudinal axis and at a plurality of lateral measurement locations along the second lateral axis.

Other features and advantages of the invention will be apparent from the following specification taken in conjunction with the following drawings.

BRIEF DESCRIPTION OF THE DRAWINGS

To understand the present invention, it will now be described by way of example, with reference to the accompanying drawings in which.

DETAILED DESCRIPTION OF THE PREFERRED EMBODIMENT

Figure 1:
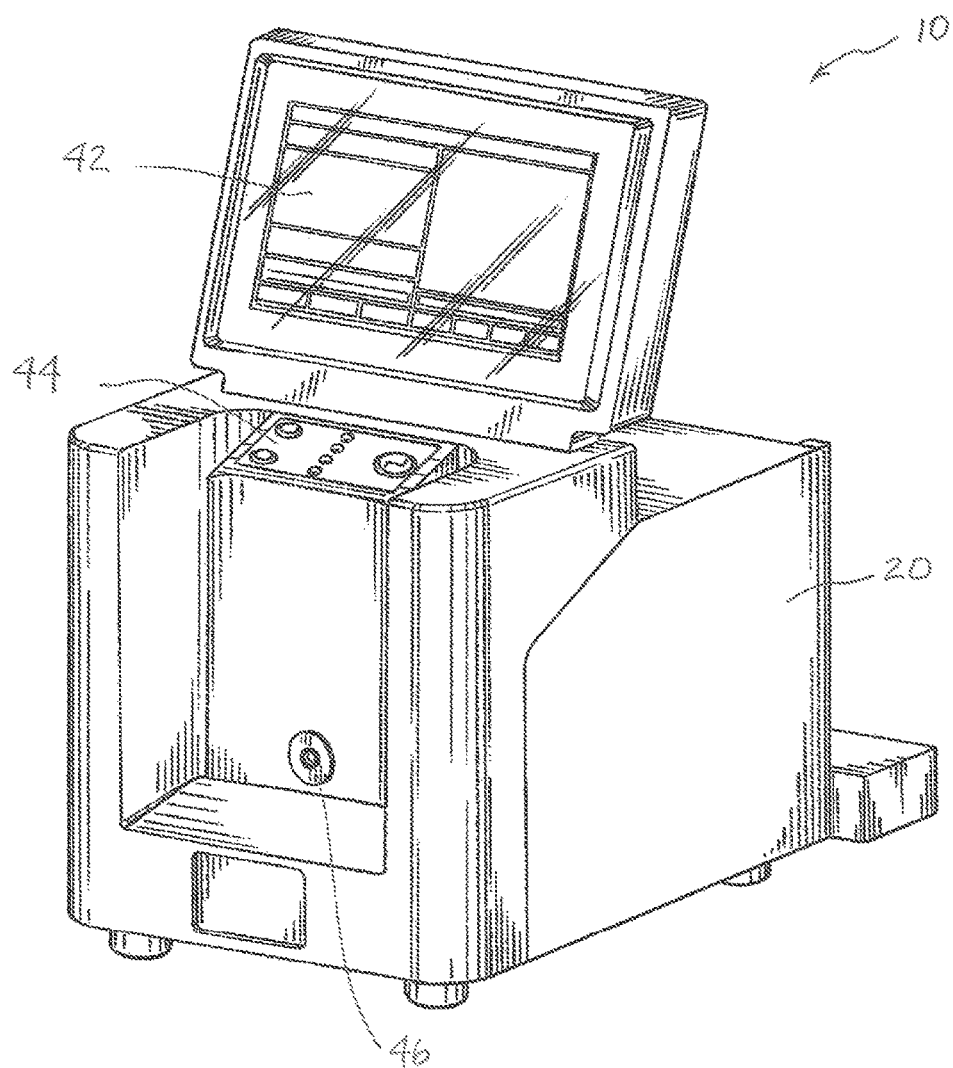
FIG. 1 is a perspective view of an ellipsometer apparatus according to an exemplary embodiment of the invention.

While this invention is susceptible of embodiments in many different forms, there are shown in the drawings and will herein be described in detail preferred embodiments of the invention with the understanding that the present disclosure is to be considered as an exemplification of the principles of the invention and is not intended to limit the broad aspect of the invention to the embodiments illustrated.

Referring to the drawings, FIG. 1 discloses a perspective view of an ellipsometer apparatus according to an exemplary embodiment of the present invention, generally designated with the reference numeral 10. As shown in FIGS. 1-5, the ellipsometer 10 generally includes a light source assembly 12, a specimen holder 14, a positioning assembly 16 and a controller 18. It is understood that the various components of the ellipsometer 10 are contained and/or supported by a housing 20. Thus, as further shown in FIG. 1, the housing 20 of the ellipsometer 10 forms a chamber for many of the various components as described herein.

Figure 2:
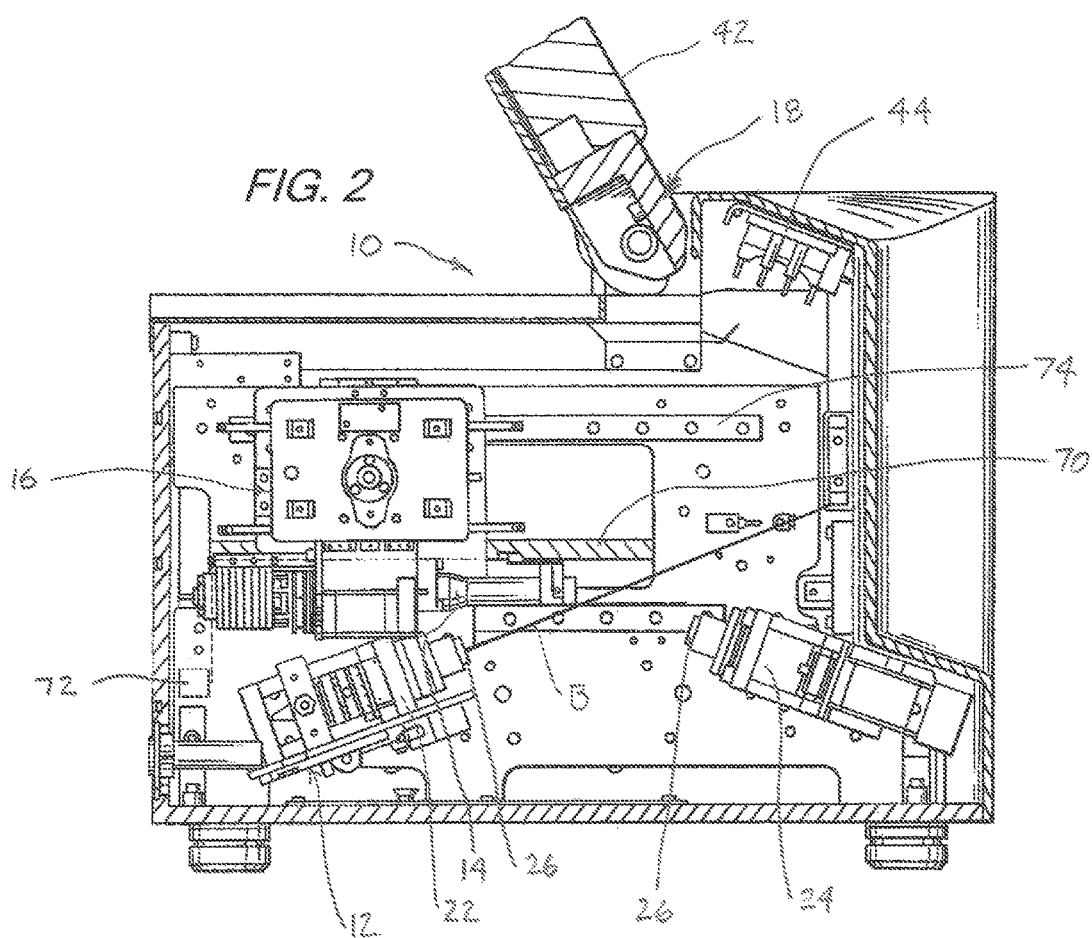
FIG. 2 is a side elevation view of the ellipsometer apparatus of FIG. 1.
Figure 3:
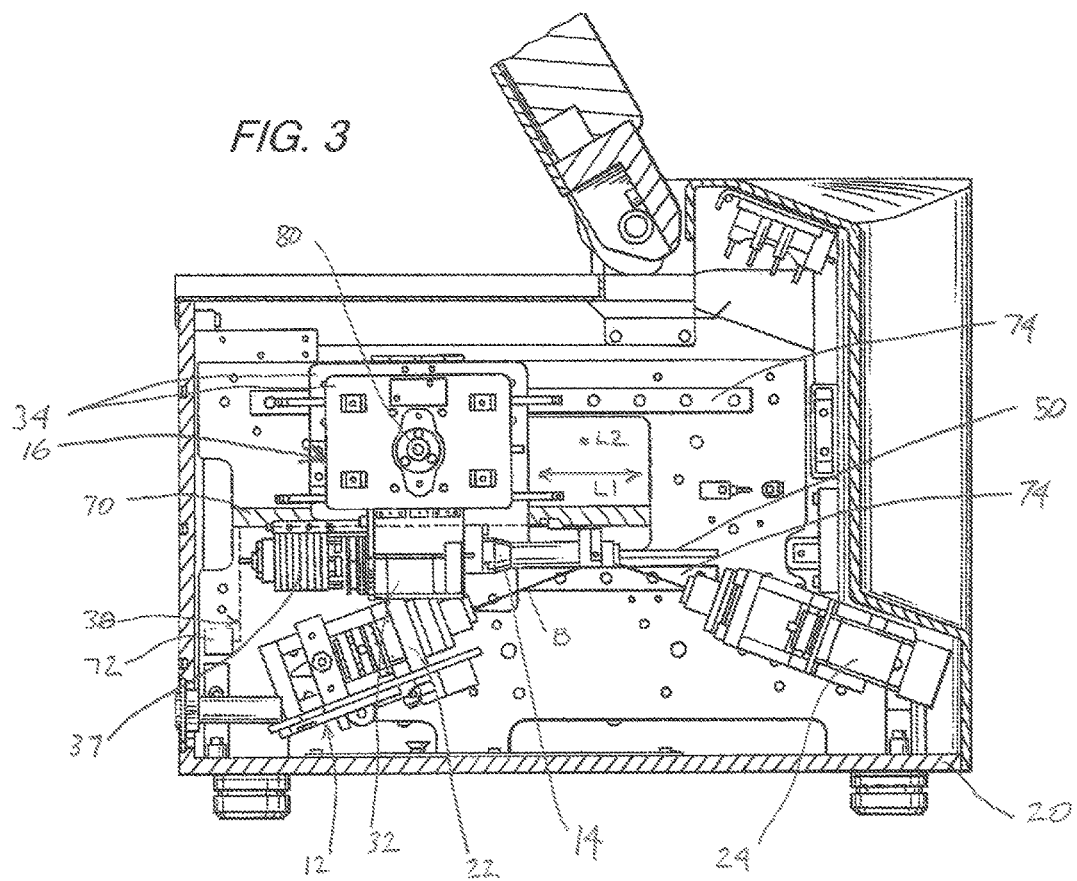
FIG. 3 is another side elevation view of the ellipsometer apparatus of FIG. 1 and having a tube specimen therein.
Figure 4:
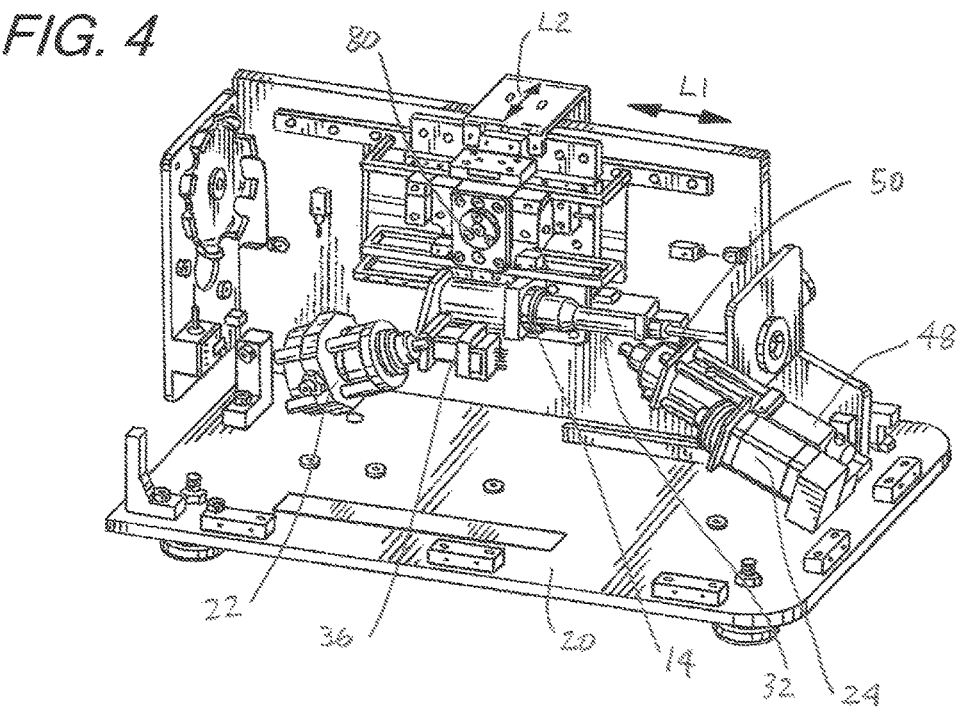
FIG. 4 is a schematic view of internal components of the ellipsometer apparatus of FIG. 1 including a positioner assembly and a light source assembly.
Figure 5:
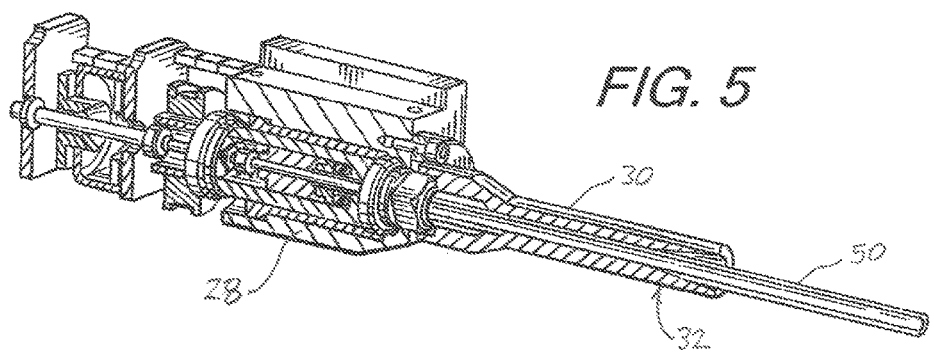
FIG. 5 is a perspective view of a specimen holder used in the ellipsometer apparatus of FIG. 1.

FIGS. 2-4 disclose the light source assembly 12. In an exemplary embodiment, the light source assembly 12 is a laser-based assembly. The assembly 12 has a laser emitter 22 and a laser receiver 24. The laser emitter 22 is mounted proximate a rear of the housing 20 and at an upward angle to be configured to project a light beam at a specimen sample to be described. The laser receiver 24 is mounted proximate a front of the housing 20 and at angle to be in position to receive a deflected beam of light from the specimen sample to be described. It is understood that a polarizer member 26 is mounted on an end of both the laser emitter 22 and the laser receiver 24 to assist in projecting and receiving the beam of light as is known in the art. As explained in greater detail below, the laser emitter 22 and the laser receiver 24 cooperate to provide a polarization of light that interacts with the specimen sample that can be analyzed to determine film properties on a test surface of the specimen sample such as film thickness. While lasers emitting and receiving laser beams are used in an exemplary embodiment, it is understood that other types of light sources such as LEDs can also be used for the light source assembly. In addition, laser emitters having varying wavelengths could be used as known in the art.

FIGS. 2-5 disclose the specimen holder 14. The specimen holder 14 has a mounting structure 28 and a receiver 30. The mounting structure 28 is structured to be operably connected to the positioning assembly 16. The receiver 30 is connected to and extends from the mounting structure 28. The receiver 30 is configured to receive the specimen sample, or specimen member, that is in the form of a cylindrical tube to be described. The receiver 30 has a generally curvilinear outer surface and also has a slot 32 wherein light from the laser emitter 22 can reach the specimen sample and be deflected to the laser receiver 24.

FIGS. 2-4 disclose the positioning assembly 16. The positioning assembly 16 has a base member 34 operably connected to a plurality of directional positioners. The positioning assembly 16 has a rotary positioner 36 that generally takes the form of a rotary motor 36 that is operably connected to the specimen holder 14. The rotary motor 36 is configured to rotate the specimen sample within the specimen holder 14 to allow for ellipsometer analysis/measurements/readings around an entire circumference of the sample specimen. A clamping mechanism 37 is also operably connected to the specimen holder 14 to secure the specimen sample within the holder 14. The positioning assembly 16 further has a first positioner 38 and a second positioner 40.

Figure 12:
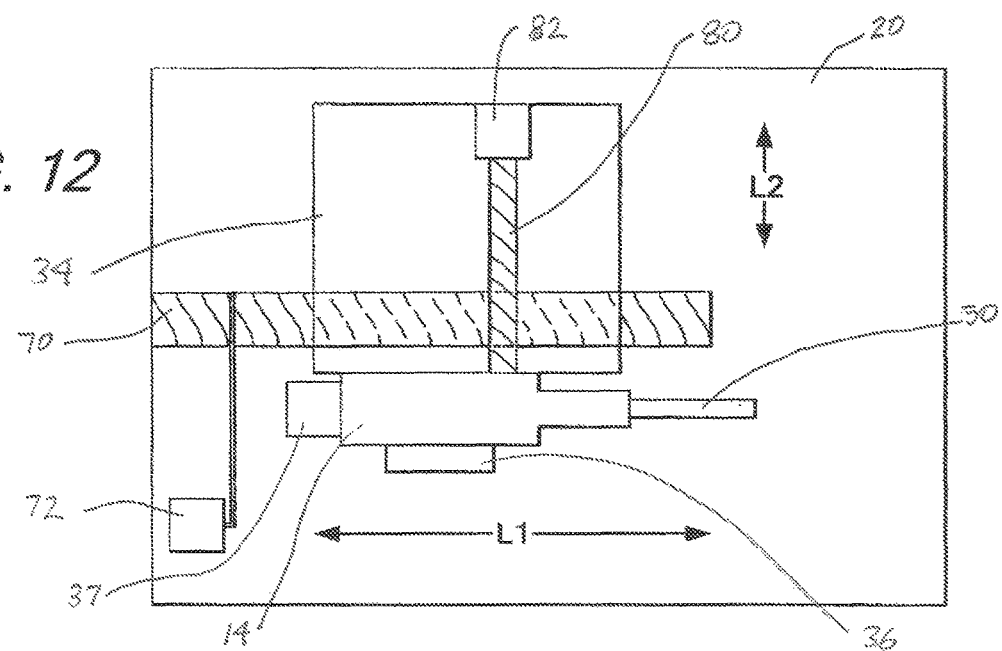
FIG. 12 is schematic top plan view of the ellipsometer apparatus of FIGS. 1-4 showing additional features of a positioner assembly of the apparatus; and, FIGS. 13A-13C are schematic views of the specimen sample and showing measurement locations and groupings.

The first positioner 38 is capable of moving the specimen holder 14, and therefore the specimen sample, along a first axis L1 generally between a front portion of the housing 20 and a rear portion of the housing 20, which may be referred to as a longitudinal axis. It is understood that the first positioner 38 has a first lead screw 70, or servo shaft, operably connected to a first positioning motor 72. Additional support rails 74 may be provided where the base 34 rides along the rails 74. FIGS. 2 and 3 show a pair of support rails 74 in an upper and lower configuration. Additional support rails could also be utilized. The base 34 is operably connected to the first lead screw 70. The first positioning motor 72 rotates the first lead screw 70 wherein the base 34 and therefore the specimen holder 14, through additional operable connections via the second positioner 40 to be described, moves longitudinally along the axis L1. Thus, the first positioner 38, through rotation of the first lead screw 70, moves the specimen holder 14 along the first axis L1, or longitudinal axis L1, between the front and the rear of the housing 20. These connections and movements are further shown in FIG. 12.

The second positioner 40 is capable of moving the specimen holder 14, and therefore the specimen sample, along a second axis L2 generally between a first side of the housing 20 and a second side of the housing 20, which may be referred to as a lateral axis L2. It is understood from FIGS. 2-3, 7 and 12 that the second positioner 40 has a second lead screw 80 operably connected to a second positioning motor 82. The specimen holder 14 is operably connected to the second positioner 40 via the lead screw. As understood from the FIGS., the second positioner 40 and specimen holder 14 are operably connected to the base 34 that is operably connected to the first positioner 38 wherein the second positioner 40 and specimen holder 14 are moved along the first longitudinal axis L1. The second positioning motor 82 rotates the second lead screw 80 wherein the specimen holder 14 moves laterally within the housing 20 along the second lateral axis L2. It is understood that additional support rails could be provided to guide movement along the second lead screw 80 along the lateral axis L2.

From this description and FIGS. 2, 3, 7 and 12, it is understood that the first positioner 38 and the second positioner 40 are capable of moving the specimen holder 14 independently of one another. It is further understood that the first longitudinal axis L1 is generally transverse to the second lateral axis L2. Other configurations are possible as may be necessary or will benefit the film analysis performed by the ellipsometer 10. As further shown in FIGS. 2, 3 and 12, the second positioner 40 with the specimen holder 14 connected thereto is connected to the base 34 that is moved longitudinally along the first lead screw 70 and first longitudinal axis L1. The base 34 is operably connected to the first lead screw 70 and supports the second positioner 40 and specimen holder 14 for longitudinal movement along the first longitudinal axis L1. Independent of this movement, the second positioner 40 can move the specimen holder 14 along the lateral axis L2 along the second lead screw 80 as this movement is possible relative to the base 34. It is understood that the positioning assembly 16 can take other forms such as articulating arms having a suitable power source. Other robotic structures could also be provided to provide relative movement between the specimen holder 14 and the light source assembly 12. Accordingly, movement of the specimen holder 14 and therefore the specimen member 50 could be moved along other axes in addition to the first longitudinal axis L1 and the second lateral axis L2. It is further understood that the second lateral axis L2 includes a lateral axis at each longitudinal measurement location along the first longitudinal axis L1.

It is understood that the controller 18 includes multiple components to effect operability of the ellipsometer 10. The controller 18 has a display 42 and an input device 44 in the form of a keyboard 44 supported by the housing 20. It is further understood that the controller 18 also includes other components supported by the housing 20 and operably connected to the display 42 and keyboard 44 such as processors, power supplies and associated connectors including components for operable connection to a power source. It is further understood that the light source assembly 12, the positioner assembly 16 and specimen holder 14 are also operably connected to a suitable power source as necessary. The processors can include the necessary components to determine the measurements/analysis and readings from the beam of light deflected by the specimen sample. It is further understood that the motors associated with the various positioners of the positioning assembly are operably connected to the power supply and suitably supported in the housing 20.

As further shown in FIG. 1, the housing 20 generally contains the components of the ellipsometer 10 described above. The housing 20 defines a specimen inlet 46 dimensioned to receive the specimen sample when commencing operation of the ellipsometer 10. The specimen inlet 46 may further include a shutter door that opens and closes when the specimen sample is inserted and discharged from the housing 20. The ellipsometer 10 further has a photodiode assembly 48 (FIG. 4) mounted in the housing 20 that is operably connected to the controller 18.

Figure 6:
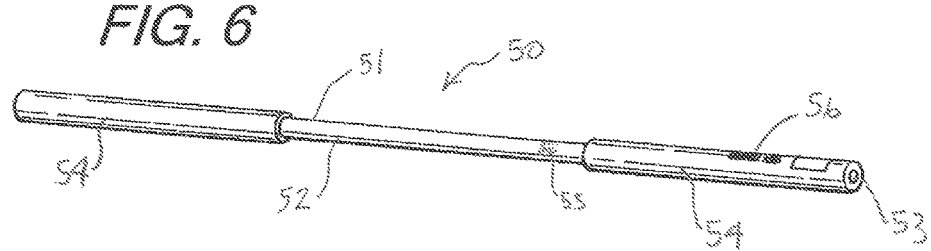
FIG. 6 is a perspective view of a specimen sample in the form of a tube used in the ellipsometer of FIG. 1.

FIG. 6 discloses the specimen sample or specimen member, generally designated with the reference numeral 50. In an exemplary embodiment, the specimen sample 50 is in the form of a metal specimen tube 50. The specimen tube 50 has a central portion 51 that defines a sample surface 52 or test surface 52. In an exemplary embodiment, the test surface 52 is cylindrical. The specimen tube 50 further has a handle end 54 on each side of the central portion 51 configured to be grasped by a user. The handle end 54 is further grasped by the specimen holder 14, and the specimen tube 50 is dimensioned to be received by the receiver 30 of the specimen holder 14. The central portion 51 is not to be grasped by a user once the specimen tube 50 is prepared with an oxidized film of jet fuel. The specimen tube 50 further has an identifier 56 thereon. The specimen tube 50 is a metal tube in an exemplary embodiment and is typically an aluminum metal tube. Other materials are also possible such as stainless steel. The metal tube 50 may also have a central channel 53 extending longitudinally through the tube. It is understood that in other exemplary embodiments, the test surface 52 can take other forms rather than the specimen tube 50.

In operation of the ellipsometer 10, it is understood that the specimen tube 50 is first prepared according to ASTM D3241, which is incorporated by reference herein. Accordingly, the specimen tube 50 is heated and jet fuel to be tested is injected over the specimen tube 50 wherein an oxidized layer of jet fuel is deposited onto the tube 50 in the form of a thin film. The thin film layer is designated schematically with the reference numeral 55 in FIGS. 6, 7 and 13A, but is deposited around a full periphery of the tube 50. Once the specimen tube 50 is properly prepared according to the testing standard, the user grasps the tube 50 at one handle end 54 and inserts the other handle end 54 into the tube inlet 46. It is understood that in preparation for insertion of the specimen tube 50, the positioning assembly 16 moves the specimen holder 14 along the longitudinal axis L1 wherein the receiver 30 is generally adjacent to the tube inlet 46 to receive the specimen tube 50. Once properly inserted wherein the specimen tube 50 is secured in the tube holder 14 via the clamping mechanism 37, the positioning assembly 16 positions the specimen holder 14, and therefore the specimen tube 50, in proper position to begin analysis by the ellipsometer 10. It is also understood the photodiode 48 will read the identifier 56 on the specimen tube 50 so the ellipsometer 10 will be able to match the measurements with the proper specimen tube 50.

FIG. 3 shows the specimen tube 50 within the specimen holder 14 in position to commence the analysis process. The laser emitter 22 projects a laser beam or light beam B to the specimen tube 50 wherein the beam B is reflected off of the tube 50 wherein the reflected beam B is ultimately received by the laser receiver 24. The laser receiver 24 and laser emitter 22 cooperate together and are operably connected to the controller 18 for proper operation of the ellipsometer 10 as is known in the art. The controller 18 receives data associated with the reflected light B to determine properties associated with the film layer of the oxidized jet fuel such as film thickness.

The ellipsometer 10 moves the specimen tube 50 via the positioning assembly 16 to analyze the film on the tube 50. It is has been determined over time that the most accurate readings/measurements are provided at the bottom center of the specimen tube 50. Thus, the laser emitter 22 is positioned to project the beam of light at the bottom center of the specimen tube 50. As discussed, the specimen tube 50 may have slight bends or distortions as a result of the tube preparation process. The slight bends and/or distortions can adversely affect the readings/measurements generated by the ellipsometer 10. This occurs as the bottom center of the specimen tube 50 is no longer aligned with the beam of light B being projected by the laser emitter 22. The ellipsometer 10 automatically compensates for such bends/distortions by moving the specimen holder 14 and specimen tube 50 laterally or side to side direction (along axis L2) via the second positioner 40 to allow for measurements to be taken laterally across the tube periphery to allow for a measurement at the bottom center of the tube notwithstanding any bend or warp of the tube 50. Prior ellipsometer designs did not provide for the capability to take lateral measurements on the tube periphery in a lateral direction on the specimen tube 50 to compensate for bends etc. of the tube 50.

Figure 13A:
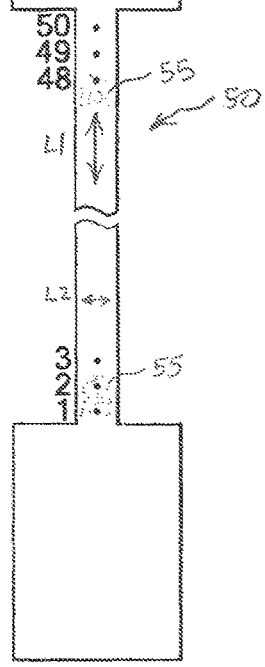
Figure 13B:
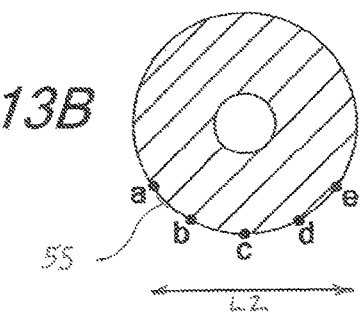

According to an exemplary process of the invention in analyzing a thin film layer on the specimen sample 50, a measurement is taken at a first longitudinal measurement location on the specimen sample 50, such as location designated "1" in FIG. 13A. The measurement is typically to determine the thickness of the film 55 at the measurement location. The laser emitter 22 projects the beam of light at the bottom center of the tube 50 and it has been determined that the measurement at the bottom center of the tube 50 provides the most accurate measurement of the film thickness. The bottom center of the tube 50 is represented by the "c" designation in FIG. 13B. As discussed, the tube could have been bent or warped during the preparation process. Thus, according to the exemplary process of the invention, the ellipsometer 10 determines a plurality of lateral film thickness measurements along the periphery of the specimen tube 50 in the lateral direction such as the lateral measurement locations designated a, b, c, d, e in FIG. 13B. As can be appreciated from FIGS. 7 and 12, the second positioner 40 moves the specimen holder 14 laterally along the axis L2 wherein measurements are taken at the plurality of the lateral measurement locations across the tube 50 in the lateral direction and represented by the locations a, b, c, d, e. This allows the ellipsometer 10 to determine the highest/greatest measurement value among the measurements determined at the locations a, b, c, d, e corresponding to the longitudinal measurement location 1. It is understood that the greatest measurement value corresponds to the high point of thickness of the film (the greatest thickness/film deposit on tube at the first measurement location 1). This is because the high point will always be closest to the laser emitter and have a greater thickness value and should correspond to the bottom center of the tube 50. If the specimen tube 50 is not bent or warped at this location 1, the high point measurement that is determined will correspond to location c and the ellipsometer 10 will use this high point measurement as an indication of the bottom center of the tube 50. However, if the specimen tube 50 is bent at the longitudinal measurement location 1, a high point measurement of film thickness will be determined at one of the other lateral locations remote from location c. e.g., a location of a, b, d or e. In such case, the ellipsometer 10 will use this other lateral measurement location as the actual bottom center of the tube 50. Thus, the ellipsometer 10 will index this other lateral measurement value to be the value used for the film thickness at the longitudinal measurement location 1. The measurement for the first longitudinal measurement location 1 is indexed to correspond to the high point measurement providing more accurate results as the measurement taken is at the true bottom center of the tube 50. It is understood that the high point measurement corresponding to the greatest film thickness may correspond to location c, or if the tube 50 is bent, will correspond to one of the other lateral measurement locations. In the latter case, the one of the other lateral measurement locations will be indexed to be the measurement used as the bottom center of the tube 50.

Figure 13C:
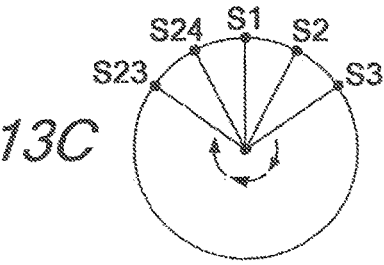

The first positioner 38, the second positioner 40 and the rotary positioner 36 cooperate to move the tube holder 14 and specimen tube 50 for the ellipsometer 10 to analyze the film layer 55 on the tube 50 around a full periphery of the tube 50. Thus, the above process is repeated a plurality of times to determine a plurality of measurements. As discussed, the ellipsometer 10 will take a plurality of measurements along the longitudinal direction of the tube. In an exemplary embodiment and as indicated in FIG. 13A, measurements are taken at fifty (50) longitudinal measurement locations. As discussed above, the first positioner 38 is utilized to move the specimen tube 50 to have measurement taken at each of these locations. At each longitudinal measurement location (e.g., 1-50), a plurality of lateral measurements are taken along the periphery of the tube 50 in the lateral direction (L2) corresponding to lateral measurement locations a, b, c, d, e. It is understood that the lateral locations can vary over the periphery of the tube 50. The second positioner 40 is utilized to move the specimen tube 50 to take these film thickness measurements at these lateral measurement locations. The group of 50 longitudinal measurements may be referred to as a "slice." FIG. 13C designates a slice S1 at a first angular position on the tube 50. The rotary positioner 36 rotates the specimen tube 50 to a new position wherein it is understood that the ellipsometer 10 takes the same set of longitudinal measurements along the longitudinal portion of the test surface 52. It is understood that the same sequence of measurements are taken at similar lateral measurement locations a, b, c, d, e at each of the next longitudinal measurement locations on the specimen tube 50, e.g. a second slice of the specimen tube 50 designated as S2 in FIG. 13C. In an exemplary embodiment, the tube is segmented such as 24 slices of measurements are taken around the full periphery of the tube 50 wherein each slice is angularly spaced 15 degrees. It is understood that the measurements can be started at the same end of the specimen tube 50 or measurements can be taken starting at the end of the tube from the end of the first slice of measurements in order to save time in the process in minimizing the amount the tube holder 14 must be moved. This can also be done regarding the lateral measurement locations to save time in moving the specimen tube 50. As discussed, the measurement process described above is repeated for multiple slices around the full periphery of the specimen tube 50. In certain exemplary embodiments, the ellipsometer 10 will take measurements for 24 slices around the specimen tube 50—S1-S24 in FIG. 13C. Thus, in one exemplary embodiment, the measurement analysis will include 1200 measurements (50 longitudinal measurements for 24 slices of measurements). It is understood the number of measurements can be increased or decreased based on the desired analysis.

Figure 9:
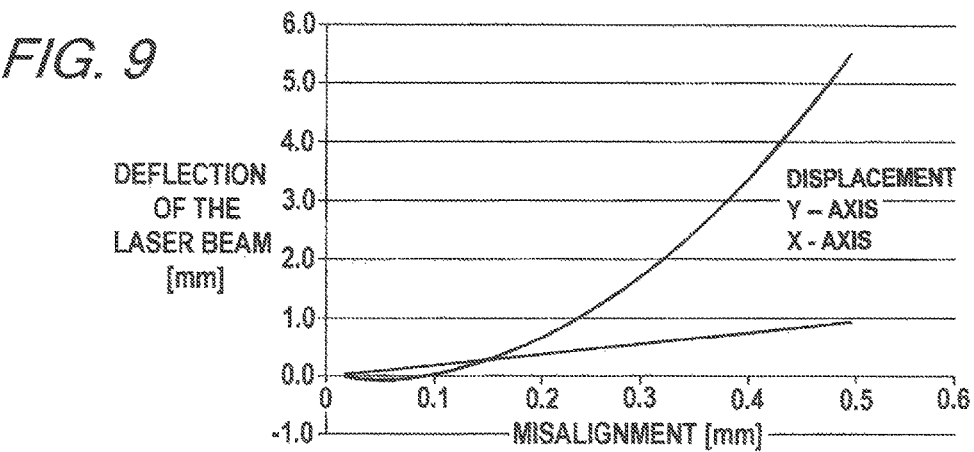
FIG. 9 is a graph showing a misalignment relationship between a laser beam and tube specimen.
Figure 10:
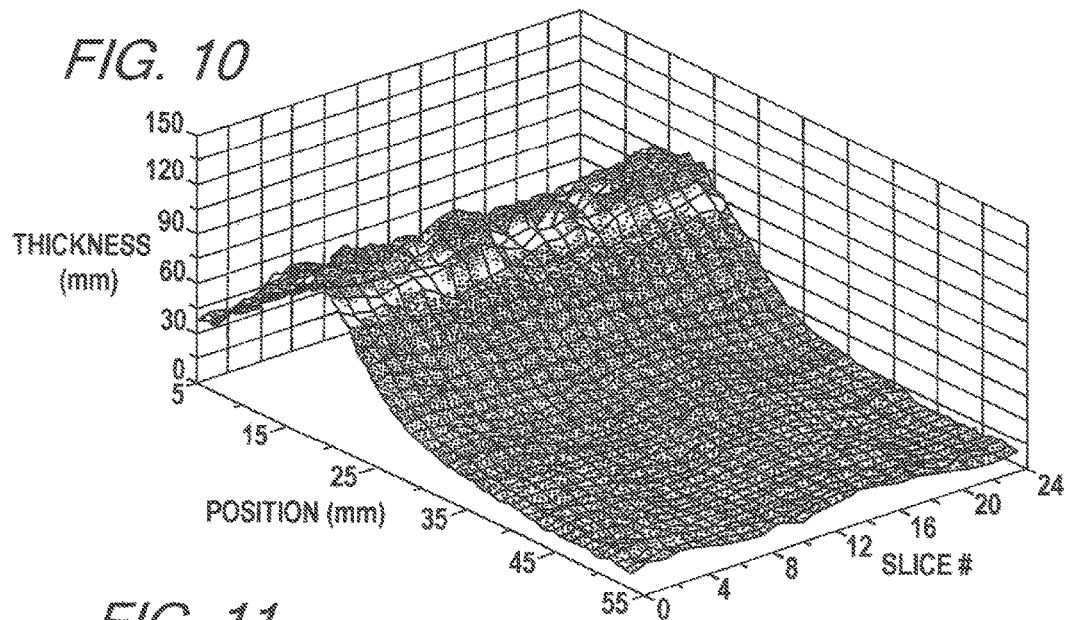
FIG. 10 is graphical representation of measurements of a thin film on the tube specimen.
Figure 11:
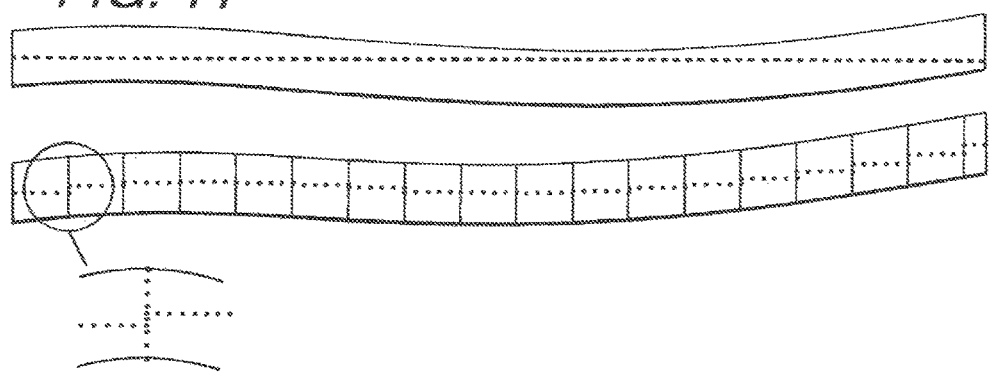
FIG. 11 is a schematic representation of measurements taken on a bent tube specimen with and without measurement compensation.

FIG. 10 shows a schematically graphical representation of measurements taken along the specimen tube 50. The measurements shown in FIG. 10 represent the film thicknesses at the longitudinal measurement locations (e.g., the 5 mm location corresponding to the longitudinal measurement location 1 in FIG. 13A and the 55 mm location corresponding to the longitudinal measurement location 50 in FIG. 13A) and for the 24 "slices" of measurements taken around the full periphery of the specimen tube 50. As discussed, the specimen tube 50 can become bent or distorted during preparation of the specimen tube 50 for measurement. Such bends or distortions can lead to inaccurate readings because the laser beam and specimen tube 50 become misaligned (when misaligned, measurements taken for the film thickness are not at the true bottom center of the tube). FIG. 9 illustrates the influence of the misalignment between the beam and the specimen tube 50. As shown, a very minute misalignment, e.g., 0.5 mm, leads to a significantly increased deflection of the laser beam. As discussed, the ellipsometer 10 can automatically compensate for these bends via the second positioner 40 and determining the proper measurement location a,b,c,d,e to be used, e.g., the actual, true bottom center of the tube 50. FIG. 11 shows a difference in measurements taken when bends exist in the specimen tube 50 with and without measurement compensation. The top measurement trace in FIG. 11 does not have all the measurements taken at the true bottom center portion of the tube as is desired. The middle measurement trace in FIG. 11 represents measurements taken with the compensation feature via the second positioner 40 of the present invention. With the multiple lateral measurements a,b,c,d,e taken as represented by the third bottom measurement trace in FIG. 11, a new bottom center point on the tube 50 is indexed for the measurement to be taken for the particular longitudinal measurement location 1-50. This new bottom center point measurement is assigned to the film thickness value at the particular longitudinal measurement location. This provides for more accurate film thickness readings and a more accurate representation of the properties of the film on the specimen tube 50.

Figure 7:
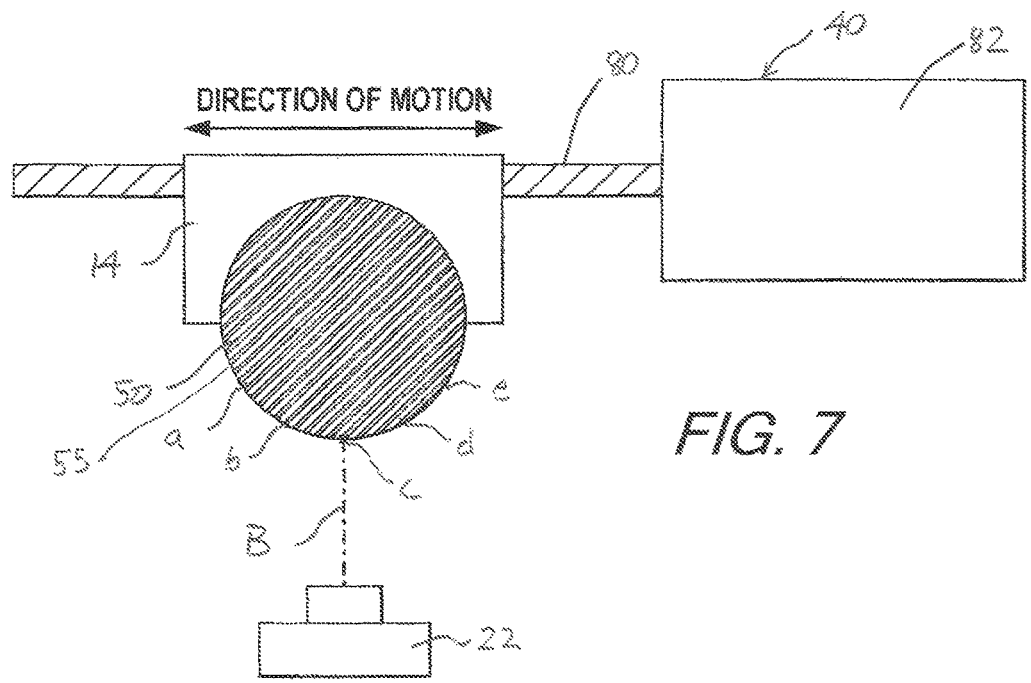
FIG. 7 is schematic view of a positioner assembly used in the ellipsometer of the present invention.
Figure 8:
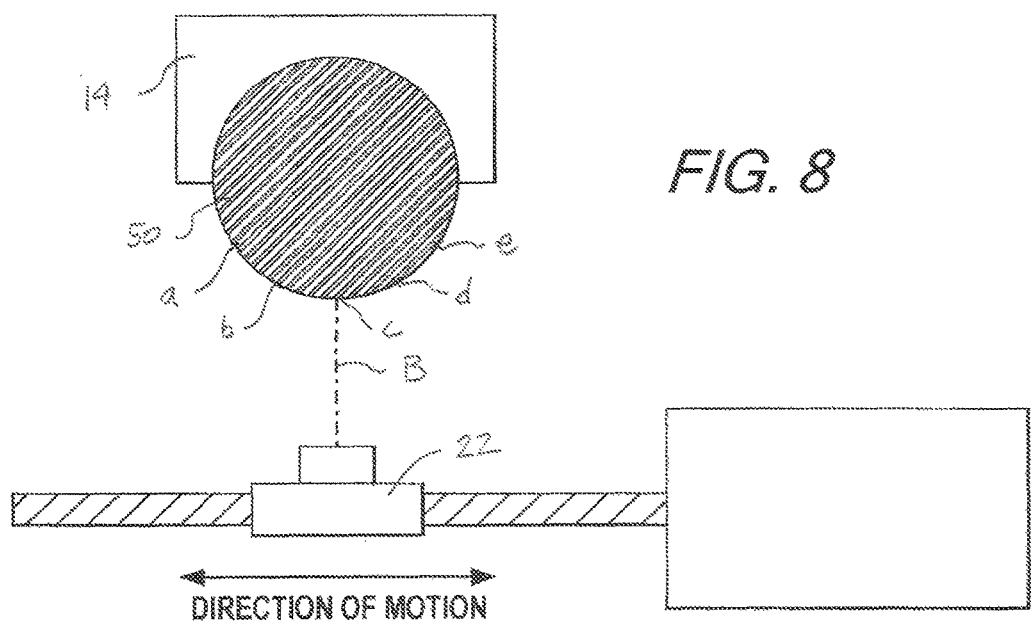
FIG. 8 is a schematic view of another positioner assembly used in the ellipsometer of the present invention.

As described herein and as can be appreciated from FIG. 7, the ellipsometer 10 provides for measurement compensation via the second positioner 40 laterally moving the specimen holder 14. This provides for automatic tube centering to index a new measurement value for the true bottom center of the tube and provide more accurate measurements and rating ability of the jet fuel. The greater accuracy is the result of the measurement taken for a respective longitudinal measurement location that corresponds to the bottom center of the tube. It is understood that relative movement between the light source assembly 12 and the specimen holder 14 and therefore the specimen tube 50 is achieved. As shown in FIG. 8, it is understood that the light source assembly 12 can be configured for movement wherein the specimen holder 14 is fixedly mounted in the housing 20. Thus, depending on the configuration used in FIG. 7 and FIG. 8, relative movement is provided between the light source assembly 12 and the specimen holder 14.

It is understood that the measurement compensation feature disclosed herein is utilized in an ellipsometer device in one exemplary embodiment of the invention. It is understood that the measurement compensation via automatic tube centering where lateral measurements are used to index to an actual bottom center tube measurement can be used in other devices such as interferometers. The invention can also be incorporated into other devices requiring analysis of a generally cylindrical specimen sample.

The ellipsometer device of the present invention provides several benefits. The ellipsometer automatically compensates for bent or distorted metal tubes measured in the thermal oxidation test according to ASTM D3241 to provide more accurate readings. This results in better thermal stability ratings of jet fuels. Also, tube straightening steps are not necessary in preparing the specimen tube for analysis by the ellipsometer, which can adversely affect the specimen tube prior to analysis. Instead, lateral measurements can be taken along the periphery of tube in the lateral direction to determine the measurement that is at the true bottom portion of the tube. Ellipsometer designs of the prior art only provided for a plurality of film thickness measurements along the longitudinal axis of the specimen tube. Such designs assumed the measurements were being taken at the bottom center of the tube. No compensation in a lateral direction was possible. With the present design, at each longitudinal measurement location, the specimen tube can be moved laterally to a plurality of lateral measurement locations to determine the film thickness at the true bottom center of the specimen tube, thus providing most accurate film thickness measurements and ratings analysis.

While the invention has been described in its preferred embodiments, it is to be understood that the words which have been used are words of description rather than limitation and that changes may be made within the purview of the appended claims without departing from the true scope and spirit of the invention in its broader aspects.

What is claimed is:

1. An ellipsometer apparatus for analyzing a film layer on a specimen member, the specimen member in the form of a specimen tube defining a cylindrical test surface on an outer surface of the specimen tube, the film layer on the outer surface of the specimen tube, the apparatus comprising:
    a light source assembly having a laser emitter and a laser receiver;
    a specimen holder configured to hold the specimen tube;
    a positioner assembly connected to the specimen holder, the positioner assembly having a first positioner capable of moving the specimen holder along a first longitudinal axis, the positioner assembly having a second positioner capable of moving the specimen holder along a second lateral axis; and
    a controller operably connected to the light source assembly and the positioner assembly wherein the laser emitter is configured to project a beam of light onto the specimen tube at a measurement location wherein the beam of light is configured to be deflected and received by the laser receiver wherein a film thickness measurement is determined by the controller, wherein a plurality of film thickness measurements are configured to be determined by the controller on the specimen tube along the longitudinal axis at a plurality of longitudinal measurement locations in response to movement of the specimen holder by the first positioner, wherein at each of the longitudinal measurement locations, a plurality of lateral film thickness measurements are configured to be determined by the controller along the lateral axis along a periphery of the specimen tube in response to movement of the specimen holder by the second positioner wherein the film thickness measurement along the lateral axis determined by the controller to be largest in value is indexed to correspond to the thickness measurement at the respective longitudinal measurement location.

2. The apparatus of claim 1 wherein the film thickness measurement along the lateral axis determined by the controller to be largest in value corresponds to the film thickness at a bottom center location on the tube.

3. The apparatus of claim 1 wherein the first positioner has a first positioner motor connected to a first lead screw, the first lead screw operably connected to the specimen holder, wherein the first lead screw is rotatable by the first positioner motor to move the specimen holder along the first longitudinal axis.

4. The apparatus of claim 1, wherein the second positioner has a second positioner motor connected to a second lead screw, the second lead screw operably connected to the specimen holder, wherein the second lead screw is rotatable by the second positioner motor to move the specimen holder along the second lateral axis, the second lateral axis being generally transverse to the first longitudinal axis.

5. The apparatus of claim 1, wherein the positioning assembly further comprises a rotary positioner operably connected to the specimen holder and configured to rotate the specimen member 360° around a central axis of the specimen tube.

6. The apparatus of claim 1 wherein a plurality of measurements taken on the specimen member along the first longitudinal axis defines a slice of measurements, and wherein measurements are taken on the specimen member corresponding to a plurality of slices around the cylindrical specimen member.

7. The apparatus of claim 6 wherein the slice of measurements comprises 50 measurements.

8. The apparatus of claim 7 wherein a first slice is angularly spaced from a second slice.

9. The apparatus of claim 6 wherein 24 slices are defined on the specimen member.

10. An apparatus for analyzing a film layer on a specimen member, the apparatus comprising:
    a light source assembly having a laser emitter and a laser receiver;
    a specimen holder holding the specimen member, the specimen member being a cylindrical specimen tube defining a cylindrical test surface on an outer surface of the specimen tube, the specimen tube having a film of oxidized jet fuel on the outer surface of the specimen tube;
    a positioner assembly connected to the specimen holder, the positioner assembly capable of moving the specimen tube along a lateral axis; and
    a controller operably connected to the light source assembly and the positioner assembly wherein the laser emitter projects a beam of light onto the test surface at a measurement location wherein the beam of light is deflected and is received by the laser receiver wherein a film thickness measurement is determined by the controller, wherein the positioner assembly is configured to move the specimen tube along the lateral axis wherein a plurality of film thickness measurements are determined by the controller along the test surface of the tube along the lateral axis.

11. An ellipsometer apparatus for analyzing a thin film on a cylindrical test surface, the apparatus comprising:

a light source assembly having a laser emitter and a laser receiver;

a specimen holder holding a specimen tube defining the cylindrical test surface on an outer surface of the specimen tube, the specimen tube having a film of oxidized jet fuel on the outer surface of the specimen tube to be analyzed;

a positioner assembly connected to the specimen holder, the positioner assembly comprising:

a first positioner having a first positioner motor connected to a first lead screw, the first lead screw operably connected to the specimen holder, wherein the first lead screw is rotatable by the first positioner motor to move the specimen holder along a first longitudinal axis, a second positioner having a second positioner motor connected to a second lead screw, the second lead screw operably connected to the specimen holder, wherein the second lead screw is rotatable by the second positioner motor to move the specimen holder along a second lateral axis, the second lateral axis being generally transverse to the first longitudinal axis, and a rotary positioner operably connected to the specimen holder and capable of rotating the specimen tube 360° around a central axis of the specimen tube; and a controller operably connected to the light source assembly and the positioner assembly wherein the laser emitter projects a beam of light onto the specimen tube at a measurement location wherein the beam of light is deflected and received by the laser receiver wherein a film thickness measurement is determined by the controller, wherein a plurality of film thickness measurements are determined by the controller on the specimen tube along the longitudinal axis at a plurality of longitudinal measurement locations in response to movement of the specimen holder by the first positioner, wherein at each of the longitudinal measurement locations, a plurality of lateral film thickness measurements are determined by the controller along the lateral axis along a periphery of the specimen tube in response to movement of the specimen holder by the second positioner wherein the film thickness measurement along the lateral axis determined by the controller to be largest in value is indexed to correspond to the thickness measurement at the longitudinal measurement location, wherein the plurality of measurements taken along the longitudinal axis of the specimen tube is defined as a slice of measurements, wherein the rotary positioner rotates the specimen tube around a full periphery of the specimen tube wherein the controller determines film thickness measurements for a plurality of slices of measurements.

12. A method of analyzing a thin film on a cylindrical test surface, the method comprising:

providing a light source assembly having a laser emitter and a laser receiver;

providing a specimen holder for holding a specimen tube defining the cylindrical test surface on an outer surface of the specimen tube, the specimen tube having a film of oxidized jet fuel on the outer surface of the specimen tube to be analyzed;

providing a positioner assembly connected to the specimen holder, the positioner assembly capable of moving the specimen holder along a lateral axis;

providing a controller operably connected to the light source assembly and the positioner assembly;

projecting a beam of light from the laser emitter onto the specimen tube at a first longitudinal measurement location wherein the beam of light is deflected to the laser receiver;

receiving the deflected beam of light by the laser receiver wherein a film thickness measurement is determined by the controller;

moving the specimen holder along the lateral axis wherein film thickness measurements are determined by the controller at a plurality of lateral measurement locations that correspond to the first longitudinal measurement location.

\* \* \* \* \*